United States Patent [19]

Bolesky

[11] 4,275,717
[45] Jun. 30, 1981

[54] INTRAMEDULLARY FIXATION DEVICE FOR FRACTURED TUBULAR BONES

[75] Inventor: Richard C. Bolesky, Warsaw, Ind.

[73] Assignee: Zimmer USA, Inc., Warsaw, Ind.

[21] Appl. No.: 61,343

[22] Filed: Jul. 27, 1979

[51] Int. Cl.³ .............................................. A61F 5/04
[52] U.S. Cl. ......................... 128/92 BC; 128/92 BA
[58] Field of Search ........... 128/92 R, 92 BC, 92 BA, 128/92 A, 92 CZ

[56] References Cited

U.S. PATENT DOCUMENTS

| 3,779,239 | 12/1973 | Fischer et al. | 128/92 BC |
|---|---|---|---|
| 3,977,398 | 8/1976 | Burstein | 128/92 BC |
| 3,986,504 | 10/1976 | Avila | 128/92 BC |

FOREIGN PATENT DOCUMENTS 2544918 5/1976 Fed. Rep. of Germany ...... 128/92 BC
575091 10/1977 U.S.S.R. .............................. 128/92 BC

*Primary Examiner*—Robert W. Michell
*Assistant Examiner*—C. W. Shedd
*Attorney, Agent, or Firm*—Richard H. Brink

[57] ABSTRACT

A fixation device adapted for use within the medullary canal of a fractured tubular bone is characterized by having a gripper unit with a plurality of outwardly concave, springy gripper fingers which can be placed under an increased force to cause the fingers to securely engage the osseous tissue surrounding the medullary canal when the device is used to maintain the fracture in compression. Force is applied to the fingers of the gripper unit by a threaded rod extending within the canal, and the rod carries a nose piece which serves both as an aid to travel of the rod through the canal and as a means for embracing the fingers of the gripper unit to disengage the fingers from the osseous tissue of the canal.

6 Claims, 8 Drawing Figures

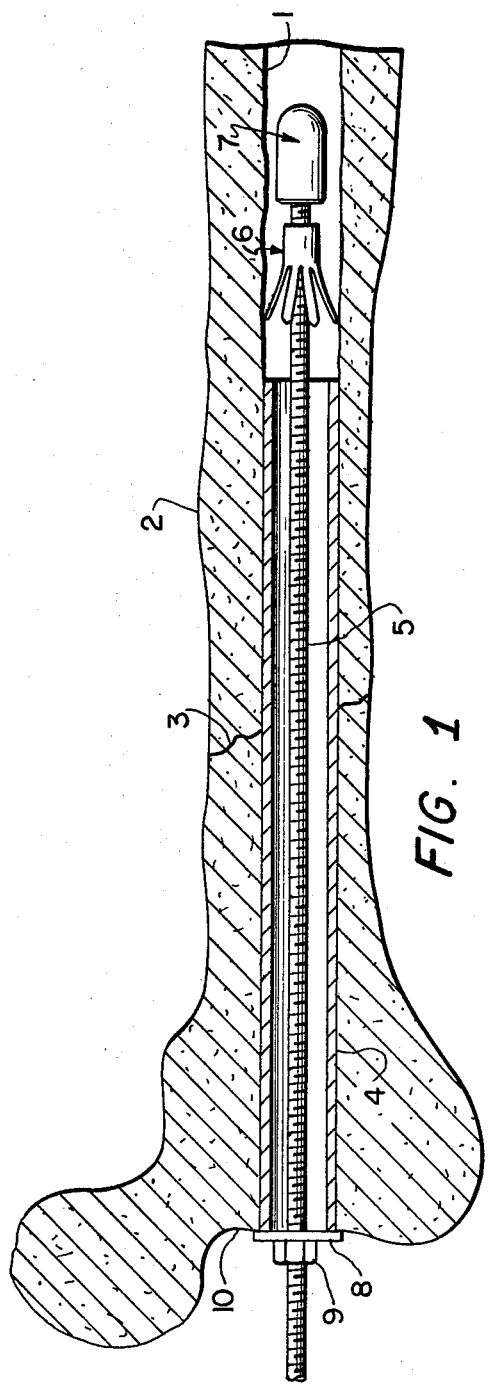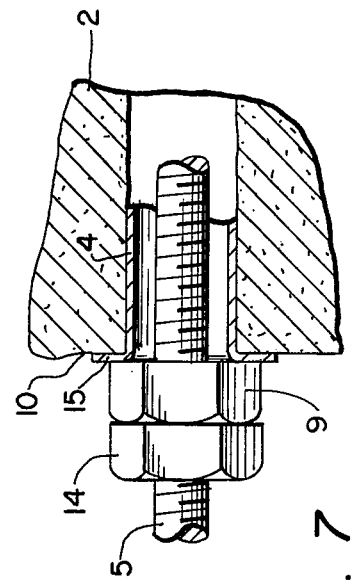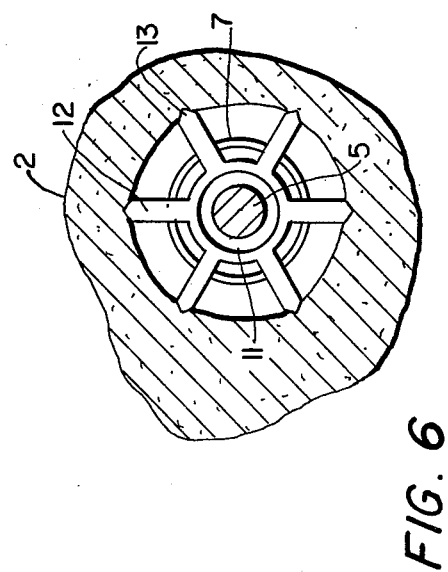

INTRAMEDULLARY FIXATION DEVICE FOR FRACTURED TUBULAR BONES

BACKGROUND OF THE INVENTION

As a result of prior art work in the treatment of bone fractures, it has been learned that a stable osteosynthesis at the fracture is obtained if the bone portions of the fracture can be secured and supported in a completely stable condition in compression or in distraction, with complete stability meaning that the bone portions involved in the fracture are held against any relative movement either longitudinally or laterally of the bone. Such prior art work has led to adoption of so-called intramedullary nails for fixation of tubular bones, and to the use of various types of stabilizing or supporting devices which operate within the medullary canal in the area of the fracture. In some such devices, the leading end of the intramedullary nail is split and the nail is equipped with a threaded rod, a threaded follower nut within the leading end of the nail operative to expand the split end, and an actuating nut and washer arrangement at the entrance of the medullary canal, as in U.S. Pat. No. 4,091,806, issued May 30, 1978 to Jacob Aginsky. In other devices, fingers carried by the nail are positively driven outwardly to engage in the wall of the medullary canal, as in U.S. Pat. No. 3,986,504, issued Oct. 19, 1976, to Rafall Avila. Though such prior art devices have achieved considerable success, there remain a number of problem areas which require further improvement.

OBJECTS OF THE INVENTION

A principal object of the invention is to devise an internal fixation device of the type described which can be operated in simple but positive fashion to engage the bone when the device is installed and disengage from the bone preparatory to removal of the device.

Another object is to provide such a device which requires only a minimum number of relatively simple parts.

A further object is to provide for application of controlled positive gripping forces as a result of a simple manipulation accomplished from outside of the bone.

A still further object is to provide such a device for supporting the fracture in compression with the compression forces being uniform about the entire peripheral extent of the fracture.

SUMMARY OF THE INVENTION

Internal fixation devices according to the invention are especially suitable for installation within the medullary canal of a fractured hollow bone, such as the femur or the tibia, and comprise a rod having a leading end portion and a trailing end portion, with at least the leading end portion being threaded, a hollow nose member secured to the leading end portion of the rod and comprising a wall surrounding the leading end portion of the rod to define a cavity which opens toward the trailing end of the rod; a gripper unit comprising a threaded hub engaged with the leading end portion of the rod, and a plurality of outwardly concave, springy, resilient gripper fingers evenly spaced about and extending both outward from the periphery of the hub and generally toward the trailing end of the rod. The fingers have pointed free ends adapted for penetrating engagement with the osseous tissue surrounding the medullary canal; and adjustable means connected to the trailing end portion of the rod to coact with the bone to apply force to the rod tending to move the rod, and therefore the gripper unit toward the entrance of the canal so that pressure is applied to the gripper fingers to bow the fingers resiliently and force the fingers to penetrate the osseous tissue of the canal. The adjustable means for applying force to the rod is typically a nut working on threads on the rod and coacting with, e.g., a washer or a flanged end of an intramedullary nail to force the washer or flange against the bone. When the device is to be removed, the nut or other adjustable means is operated to remove the force from the rod, and the rod is then turned in a direction to cause the coacting threads at the hub of the gripper unit to cause the rod to move longitudinally until the nose member embraces the gripper fingers, disengages the gripper fingers from the osseous tissue of the canal, and then forces the fingers inwardly into positions such that the fingers will not engage the wall of the canal as the device is withdrawn. Best results are obtained when the device is used in conjunction with an annular stabilizing means surrounding the rod, the conventional intramedullary nails being especially suitable.

DRAWINGS

In order that the manner in which the foregoing and other objects are achieved can be understood in detail, one particularly advantageous embodiment of the invention will be described with reference to the accompanying drawings, which form part of the original disclosure of this application, and therein:

FIG. 1 is a view, partially in longitudinal cross-section and partly in side elevation, of an internal fixation device according to the invention; the fixation device being shown in place in the medullary canal of a fractured bone;

FIG. 6 is a transverse sectional view taken generally on line 6—6, FIG. 3; and

FIG. 7 is an enlarged fragmentary view, partly in longitudinal cross-section and partly in side elevation, illustrating a modified adjustable means for tensioning the rod of the device shown in FIGS. 1-6.

DETAILED DESCRIPTION OF THE INVENTION

Figure 2:
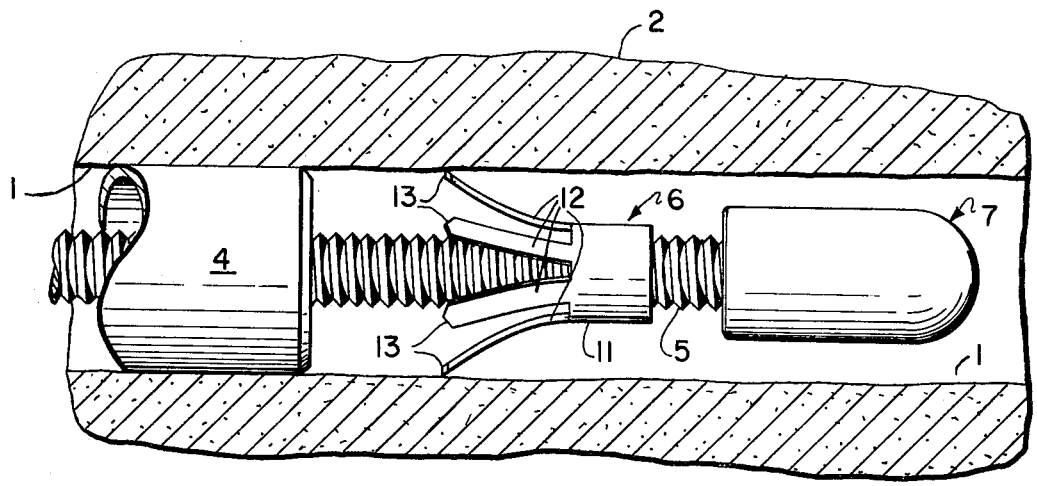
FIG. 2 is a view, similar to FIG. 1 but enlarged with respect thereto, illustrating typical positions of the gripper unit and nose member when the fixation device has been first inserted.
Figure 3:
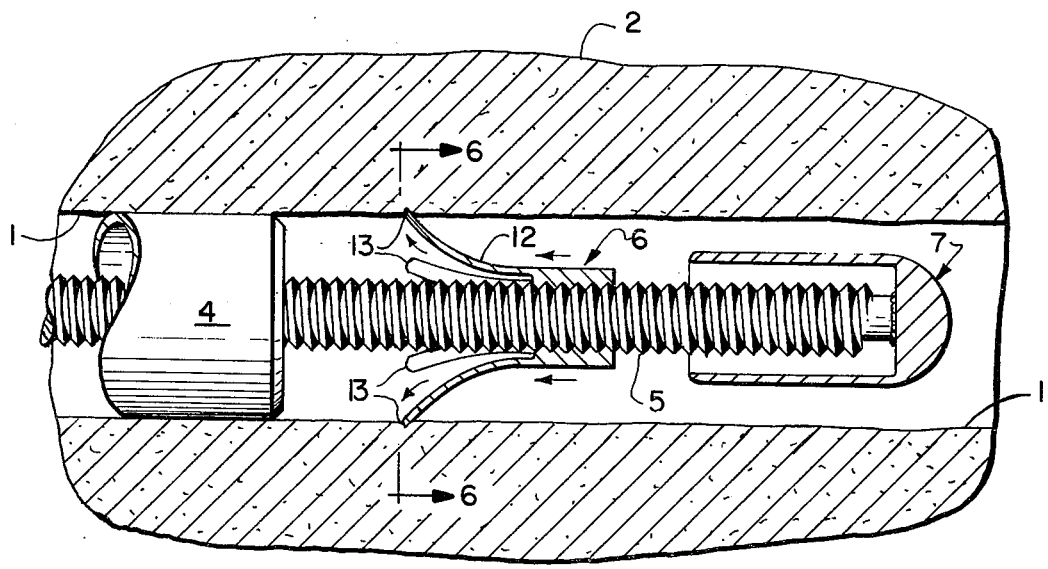
FIG. 3 is a view similar to FIG. 2 but showing the gripper device after actuating force has been applied to the rod of the device.
Figure 4:
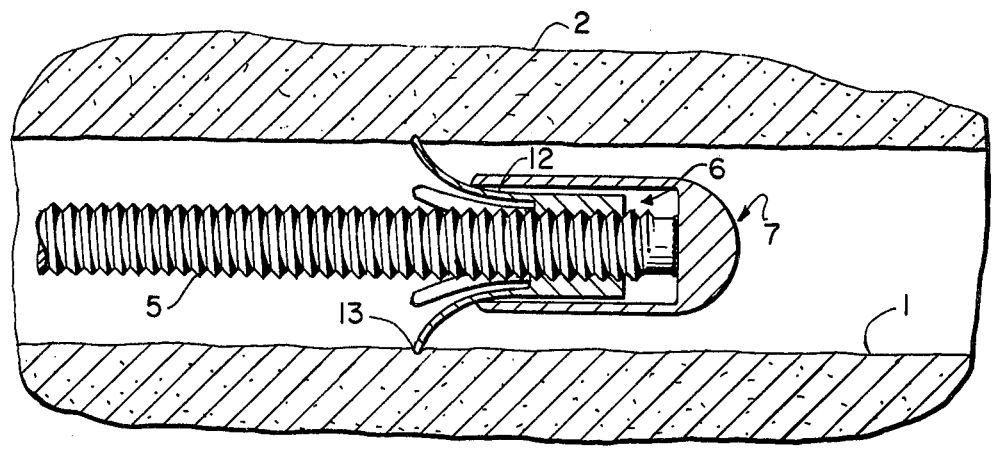
FIGS. 4 and 5 are views similar to FIG. 3 but showing two successive positions of the nose member and gripper unit during preparation for withdrawal of the internal fixation device from the medullary canal after the intramedullary nail has been removed.
Figure 5:
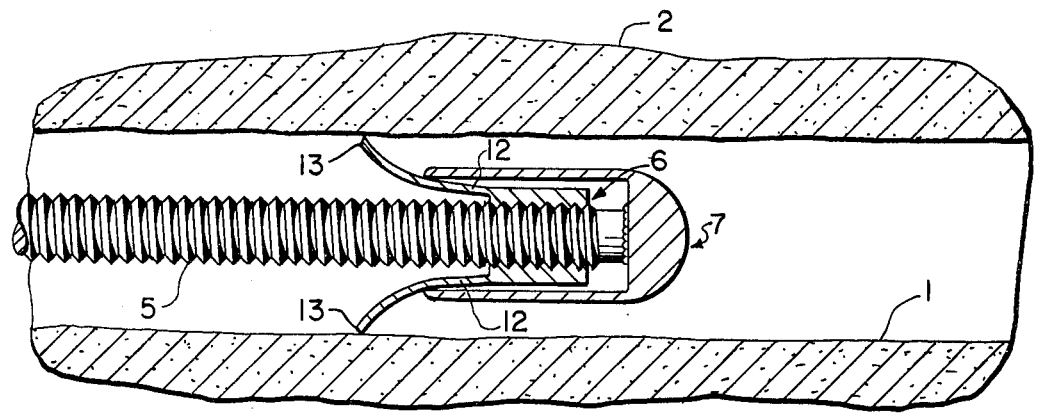
Figure 8:
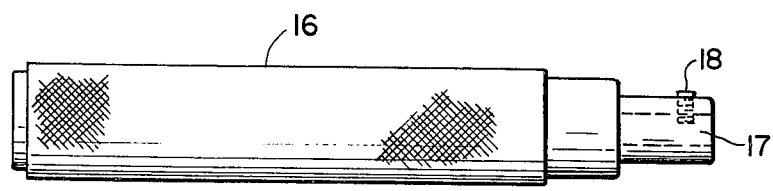
FIG. 8 is a longitudinal view of the handle which is attached to the rod for rotation of the rod.

FIGS. 1-6 illustrate a fracture fixation device according to the invention in place in the medullary canal 1 of a femur 2 which has been fractured at 3. Before installation of the fixation device, canal 1 is reamed conventionally. The subcombination of a threaded rod 5, a gripper unit 6 and a nose member 7 is then inserted through the bored entrance into the medullary canal with the gripper unit 6 being well beyond the fracture 3.

An open ended intramedullary nail 4 is then inserted over the rod 5 so that the nail extends from the entrance of the canal to a point well beyond the fracture 3 to facilitate stabilization, as seen in FIG. 1.

In this embodiment, rod 5 is threaded throughout its length, nose member 7 is secured to the leading end of the rod, and gripper unit 6 is initially disposed on the leading end portion of the rod in a location near the nose member. In this embodiment, the device is completed by a washer 8 and nut 9, FIG. 1, which, as later explained, constitute adjustable means coacting with the adjacent end of the rod 5 and the adjacent end face 10 of the bone to apply a tensioning force to rod 5 in order to actuate gripper unit 6. The rod is of such length that, when inserted to bring both nose member 7 and gripper unit 6 well beyond the fracture 3, a substantial part of the trailing end portion of the rod projects outwardly from the entrance of the canal, as seen in FIG. 1. The projected portion may be cut off as needed above the secured nut, leaving enough rod to grip onto.

Gripper unit 6 comprises an internally threaded hub 11, which has its threads operatively engaged with the threads of rod 5, and a plurality of outwardly concave, springy resilient gripper fingers 12 which are equally spaced in a circular series concentric with the rod and which extend both outward from the periphery of the hub and generally toward the trailing end of the rod. The fingers 12 have pointed free ends adapted for penetrating engagement with the osseous tissue surrounding the medullary canal. The fingers 12 are elongated thin elements of a circumferential width substantially greater than the radial thickness of the fingers, as shown in FIG. 2. When relaxed and undistorted, fingers 12 curve outwardly away from the rod so that the tips 13 of the fingers lie in a circle of slightly larger diameter than that of the reamed medullary canal. In this embodiment, the fingers 12 are integral with hub 11, with the root portions of the fingers thus being maintained in precise positions relative to rod 5 whether the fingers be relaxed or resiliently stressed. When the device is installed, the tips 13 of the fingers simply ride first along the inner wall of the reamed medullary canal 1, as seen in FIG. 2. Resilience of the fingers allow them to flex inwardly and, at this stage, there is only a small spring force urging the fingers into engagement with the osseous tissue of the canal.

The intramedullary nail 4 is then inserted over rod 5 so that the outer surface of the nail 4 is in contact with the osseous tissue of the canal and so that the nail 4 extends from the entrance to the canal to a point well beyond the fracture 3 to facilitate stabilization, as seen in FIG. 1. The nail 4 does not extend as far as the gripper unit 6, as seen in FIG. 1, and therefor does not operatively engage any portion of the gripper unit 6 or the nose member 7.

After the device has been installed in the bone, nut 9 is turned until washer 8 is snug against the end face of the bone, and the nut is then turned further, through a predetermined angular distance, to move rod 5 and gripper unit 6 a predetermined small distance toward the entrance of the canal. Tightening of the nut thus actuates gripper unit 6 into the fully engaged condition shown in FIGS. 3 and 6. As the nut is tightened, movement of gripper unit 6 to the left, as viewed in FIGS. 2 and 3, causes the tips 13 of the fingers to penetrate the wall of canal 1. As such penetration increases, the fingers 13 resist further movement of the gripper unit relative to the bone, and, with tightening of the nut still causing hub 11 to move, a force is developed which tensions rod 5 and axially compresses fingers 12, so that, with the bone resisting penetration by the fingers, a progression bowing of the resilient fingers results.

The resilient force created by the tightening of the nut 9 against the washer 8 and bone interface 10 in action with the gripper unit penetrating the medullary canal distal to the fracture site effects a positive compressive force at the fracture site. This force at the fracture site exerts uniform compression on the entire perimeter of the fracture line and secures the bone in a stable condition which promotes osteosynthesis.

Once the device is in place with the appropriate amount of pressure exerted as stated above, the wound is closed following standard surgical technique. Said device remains in place until the fracture has completely healed.

Removal of the internal fixation device is begun by loosening nut 9, thus relieving the pressure. The nut 9 and washer 8 are removed from the threaded rod 5. The nail 4 is removed from the canal 1 by pulling it out using appropriate conventional extraction equipment through the opening in the end face of the bone 10. The handle 16 is then assembled onto the trailing end of the threaded rod 5 by inserting the rod into the cannulation 17 in handle 16 and securing the rod by the use of the set screw 18. The threaded rod is rotated so that the rod moves through the threaded hub 11 of the gripper unit causing the nose member to move in a direction toward the gripper unit 6 which is still engaged with the osseous tissue of the medullary canal 1. The nose member then moves over the hub and the attached ends of the fingers on the gripper unit 6. At this point, a force may be exerted on the rod by pushing the rod 5 in a direction into and parallel to the medullary canal 1 which helps relax the bow of the fingers 12 of the gripper 6 so they disengage from the inner wall of the medullary canal 1 with minimal tissue damage. Upon further rotation of the threaded rod 5, the nose member 7 covers the gripper unit 6 and collapses the fingers 12 to the point at which they are no longer exerting pressure on the osseous tissue of the medullary canal 1, and therefore the nose member 7 can no longer move in relation to the gripper device. The rod is then withdrawn gently toward the open end face of the bone 10 until the whole assembly is removed from the canal.

A further embodiment of the invention involves the addition of a flared end 15 integrally formed with and extending radially outward of the trailing end of the nail 4 as shown in FIG. 7. The flared end 15 prevents the nail 4 from slipping into the medullary canal 1. The flared end 15 would also facilitate gripping and therefore removal of the nail 4 from the canal 1. Use of the flared end 15 eliminates the need for the washer 8.

Another embodiment of this invention is the additional use of a jam nut 14 on top of the first nut 9 to assure against any loosening of the nuts which would lessen the pressure at the fracture site. This is a modification of the adjustable tensioning means which was described in the preferred embodiment.

This device is to be made out of a biocompatible material, such as 316 Stainless Steel. While this invention has has been described and exemplified in terms of its preferred embodiment, those skilled in the art can appreciate that modifications can be made without departing from the spirit and scope of this invention.

What is claimed is:

1. In an internal fixation device for fractured tubular bones, the combination of:
   (a) a rod having a leading end portion and a trailing end portion,
   the length of the rod being such that the rod can be inserted through a bored entrance, leading-end-first, into the medullary canal of the fractured bone so as to position the leading end portion beyond the fracture when the trailing end portion is adjacent the entrance of the canal,
   at least the leading end portion of the rod being threaded;
   (b) a hollow, generally cup-shaped nose member secured to the leading end portion of the rod and comprising a wall surrounding the leading end portion of the rod to define a cavity opening toward the trailing end of the rod;
   (c) a gripper unit comprising
   an internally threaded hub having its threads operatively engaged with the threads of the leading end portion of the rod, and
   a plurality of outwardly concave, springy, resilient gripper fingers evenly spaced about and extending both outward from the periphery of said hub and generally toward the trailing end of the rod, said fingers having pointed free ends adapted for penetrating engagement with the osseous tissue surrounding the medullary canal; and
   (d) adjustable means operatively connected to the trailing end portion of the rod adapted for coacting with the bone to apply to the rod a force tending to move the leading end portion of the rod toward the entrance of the canal;
   whereby, this movement of the rod, and therefor the hub, toward the entrance of the canal being effective to increase the penetrating engagement of the fingers with the wall of the canal, and to cause the fingers to be increasingly bowed, thus maintaining the fracture in compression; and
   whereby, upon healing of the fracture, the device may be withdrawn when the adjustable means is adjusted to release said force, subsequent rotation of the rod in one direction while the gripper fingers are engaged with the osseous tissue of the canal and holding the hub against rotation which causes longitudinal movement of the nose member, which member acts as a gripper unit collapsing member, toward the gripper unit until the nose member engages the gripper unit and collapses the fingers to the extent at which said pointed ends are no longer engaged with and exerting pressure on, the osseous tissue of the canal, thereby allowing withdrawal of the fixation device from the canal.

2. The combination defined in claim 1 and further comprising an annular stabilizing means surrounding the rod, the outer surface of the annular stabilizing means being in contact with the osseous tissue of the medullary canal, and wherein the annular stabilizing means extends from the entrance of the canal to a point well beyond the fracture to facilitate stabilization, but does not extend as far as the gripper unit, and therefor does not operatively engage any portion of the gripper unit or the gripper unit collapsing member.

3. The combination defined in claim 2, wherein the annular stabilizing means is a tubular intramedullary nail.

4. The combination defined in claim 3, wherein the tubular intramedullary nail has a flared end adjacent to and extending radially outward from the trailing end portion of the rod;
   the trailing end portion of the rod is threaded; and
   the adjustable means is a nut member in threaded engagement with the trailing end portion of the rod and dimensioned to engage the flared end of the intramedullary nail to urge the same against the bone at the bored entrance of the medullary canal.

5. The combination defined in claim 1, wherein the gripper unit is an integral piece; and the gripper fingers are elongated thin elements of a circumferential width substantially greater than the radial thickness of the fingers, the gripper fingers being spaced apart equally in a circular series concentric with the longitudinal axis of the hub.

6. The combination defined in claim 5, wherein
   the hub of the gripper unit has a cylindrical outer surface; and
   the outer surfaces of the end portions of the fingers joined to the hub constitute extensions of the outer surface of the hub.

* * * * *